United States Patent
Liu et al.

(10) Patent No.: US 12,195,570 B2
(45) Date of Patent: Jan. 14, 2025

(54) DENTURE MATERIAL HAVING ANTI-MICROBIAL PROPERTIES

(71) Applicant: James R. Glidewell Dental Ceramics, Inc., Newport Beach, CA (US)

(72) Inventors: Maggie Xiaoxia Liu, Lake Forest, CA (US); Bharathy Thaiyalan, Lake Forest, CA (US); Reid Baker, Aliso Viejo, CA (US); Nicole Lee Miller, La Habra, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 18/344,480

(22) Filed: Jun. 29, 2023

(65) Prior Publication Data

US 2023/0348647 A1    Nov. 2, 2023

Related U.S. Application Data

(63) Continuation of application No. 16/936,059, filed on Jul. 22, 2020, now Pat. No. 11,708,442.

(60) Provisional application No. 62/876,893, filed on Jul. 22, 2019.

(51) Int. Cl.
| | |
|---|---|
| *A61K 31/7016* | (2006.01) |
| *A61C 13/20* | (2006.01) |
| *A61K 9/00* | (2006.01) |
| *C08F 2/46* | (2006.01) |
| *C08F 2/50* | (2006.01) |
| *C08F 267/06* | (2006.01) |
| *C08G 61/04* | (2006.01) |
| *C08K 3/08* | (2006.01) |

(52) U.S. Cl.
CPC ............. *C08F 267/06* (2013.01); *A61C 13/20* (2013.01); *C08K 3/08* (2013.01); *A61C 2201/00* (2013.01); *C08K 2003/0806* (2013.01)

(58) Field of Classification Search
CPC ......... A61C 13/02; A61C 13/20; A61C 13/01; A61C 13/2201; C08K 3/08; C08K 5/31; C08K 5/0058; C08K 2003/0806; A61K 6/844; A61K 6/17; A61K 6/887; C08F 265/06; C08F 222/1006
USPC ............. 523/122, 1; 522/6, 189, 184, 71, 1; 520/1
See application file for complete search history.

(56) References Cited

U.S. PATENT DOCUMENTS

| | | | |
|---|---|---|---|
| 8,889,196 B2 | 11/2014 | Xu | |
| 8,992,223 B2 | 3/2015 | Sun et al. | |
| 9,314,407 B2 | 4/2016 | Blizzard et al. | |
| 10,159,630 B2 | 12/2018 | Blizzard et al. | |
| 10,189,954 B2 | 1/2019 | Tay et al. | |
| 11,708,442 B2 | 7/2023 | Liu et al. | |
| 2004/0002557 A1 | 1/2004 | Qian | |
| 2013/0230676 A1 | 9/2013 | Blizzard et al. | |
| 2015/0299345 A1 | 10/2015 | Xu et al. | |
| 2016/0176902 A1 | 6/2016 | Tay et al. | |

FOREIGN PATENT DOCUMENTS

| | | |
|---|---|---|
| WO | 2005058253 A1 | 6/2005 |
| WO | 2013128304 A1 | 9/2013 |
| WO | 2015023934 A1 | 2/2015 |

OTHER PUBLICATIONS

Stencel et al, Properties of Experimental Dental Composites Containing Antibacterial Silver-Releasing Filler, Jun. 18, 2018, Materials, 11, 1031 (Year: 2018).*

Si-Ying Liu et al., Antimicrobial activity of a quaternary ammonium methacryloxy silicate-containing acrylic resin: a randomised clinical trial, Scientific Reports, Published online Feb. 23, 2016, doi: 10.1038/srep21882, www.ncbi.nlm.nih.gov/pmc/articles/PMC4763235/, in 21 pages.

Robert Stencel et al., Properties of Experimental Dental Composites Containing Antibacterial Silver-Releasing Filler, Materials 2018, 11, 1031, mdpi.com/journal/materials, in 27 pages.

J. Kreth et al., The Antimicrobial Effect of Silver Ion Impregnation into Endodontic Sealer against *Streptococcus mutans*, the Open Dentistry Journal, 2008, vol. 2, pp. 18-23.

Shi-Qiang Gong et al., Synthesis of antimicrobial silsesquioxane-silica hybrids by hydrolytic co-condensation of alkoxysilanes, Research Gate, Article: Jan. 2014, Journal: Polymer Chemistry, Submitted Aug. 11, 2013, in 17 pages.

Ewa Jablonska-Stencel et al. Effect of Silver-Emitting Filler on Antimicrobial and Mechanical Properties of Soft Denture Lining Material, Matereials 2018, 11, 318; doi: 10.3390/ma11020318, in 18 pages.

Gad MM, Effect of zirconium oxide nanoparticles addition on the optical and tensile properties of polymethyl methacrylate denture base material, Dovepress, published Jan. 9, 2018, vol. 2018:13, pp. 283-292.

(Continued)

*Primary Examiner* — Jessica Whiteley

(74) *Attorney, Agent, or Firm* — Klarquist Sparkman, LLP

(57) ABSTRACT

Antimicrobial polymer composite materials are disclosed that are suitable for making oral devices used in dental applications, such as denture bases. Acrylic resin composite materials comprising antimicrobial polymers and antimicrobial fillers provide reduction in common oral microorganisms after long-term aging, with reduced release rate of antimicrobial agents from the composite material. Antimicrobial polymers are prepared from compositions comprising acrylate and/or methacrylate monomers and polymerizable quaternary ammonium silicon-containing compounds.

12 Claims, 5 Drawing Sheets

(56) References Cited

OTHER PUBLICATIONS

Grzegorz Chladek et al., Effect of Storage in Distilled Water for Three Months on the Antimicrobial Properties of Poly(methyl methacrylate) Denture Base Material Doped with Inorganic Filler, PubMed Central (PMC), Published online Apr. 29, 2016, PMID 28773451, in 18 pages.

New York State Department of Environmental Conservation Letter—Registration 7/01, Silver sodium hydrogen zirconium phosphate (Antimicrobial AlphaSan RC 5000), dated Jul. 5, 2001, in 3 pages.

\* cited by examiner

Fig. 1. Antimicrobial Activity Of Denture Material With Varying Concentrations Of Antimicrobial Filler For Reducing *S. mutans*.
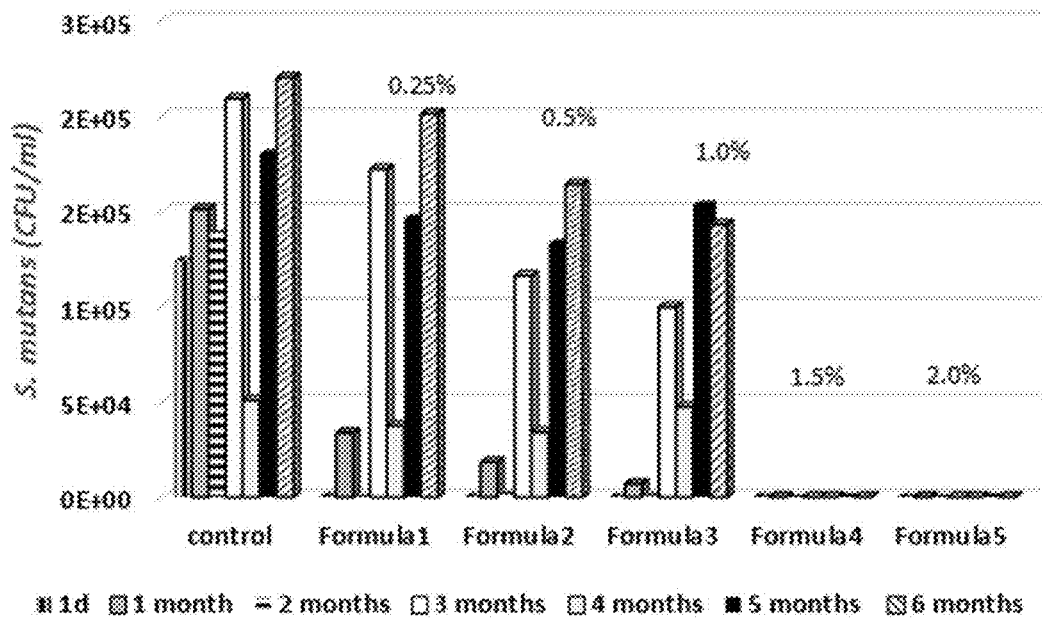
Fig. 2. Antimicrobial Activity Of Denture Material With Varying Concentrations Of Antimicrobial Filler For Reducing *C. albicans* (CFU/ml).
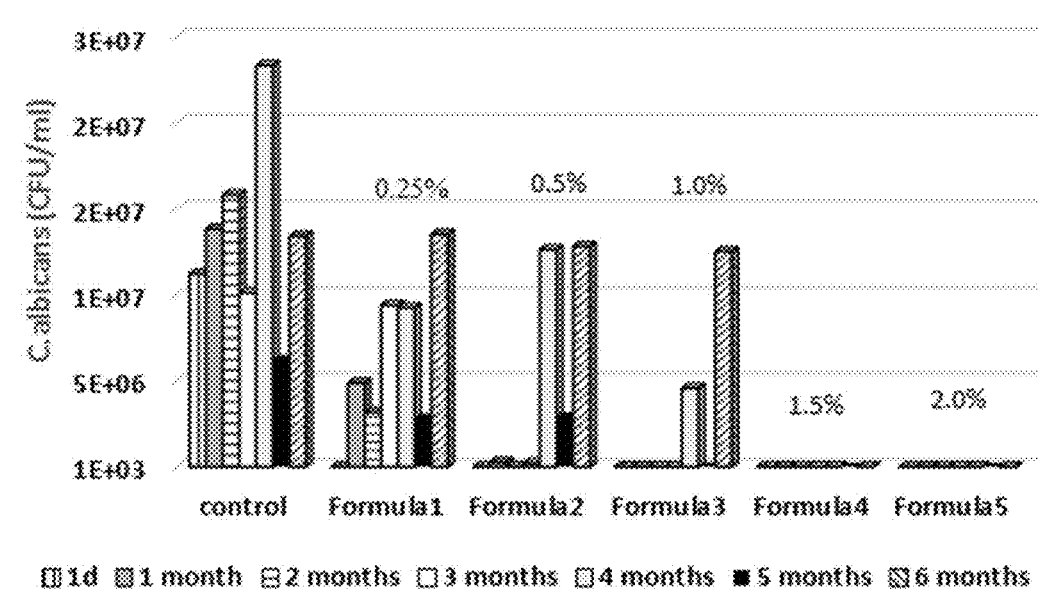

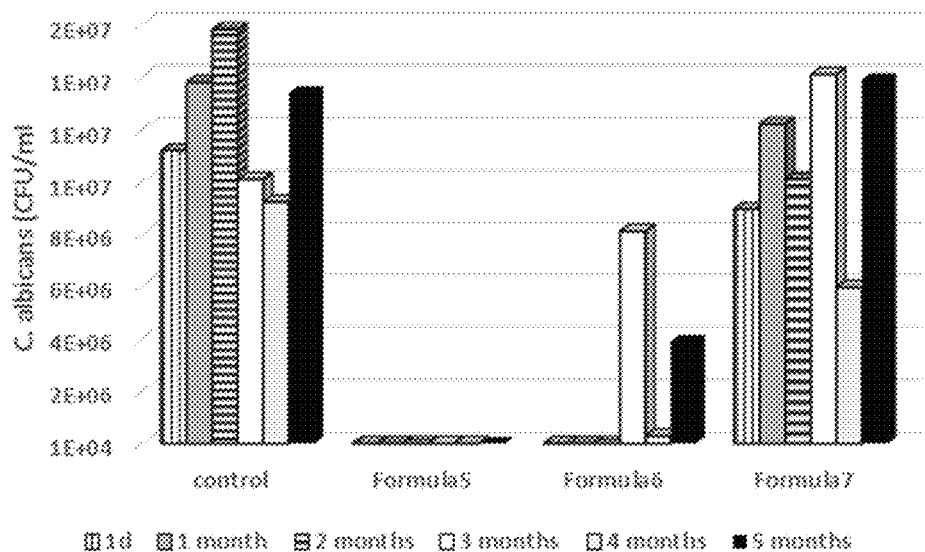
Fig. 3. Long-Term Antimicrobial Activity of Polymer Samples Tested For *C. albicans*.
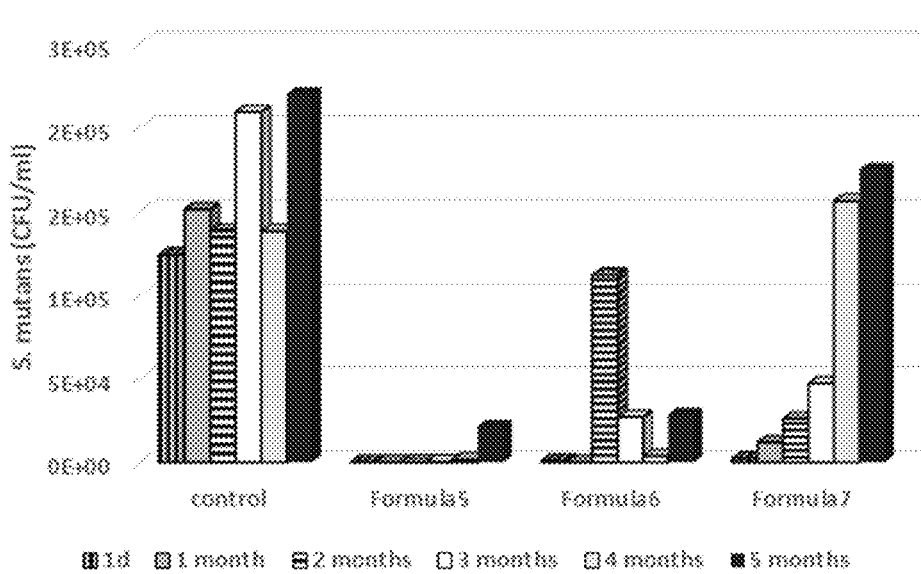
Fig. 4. Long-Term Antimicrobial Activity of Polymer Samples Against *S. mutans*.

Fig. 5. Bacterial Viability Of *S. mutans* At Four (4) Months
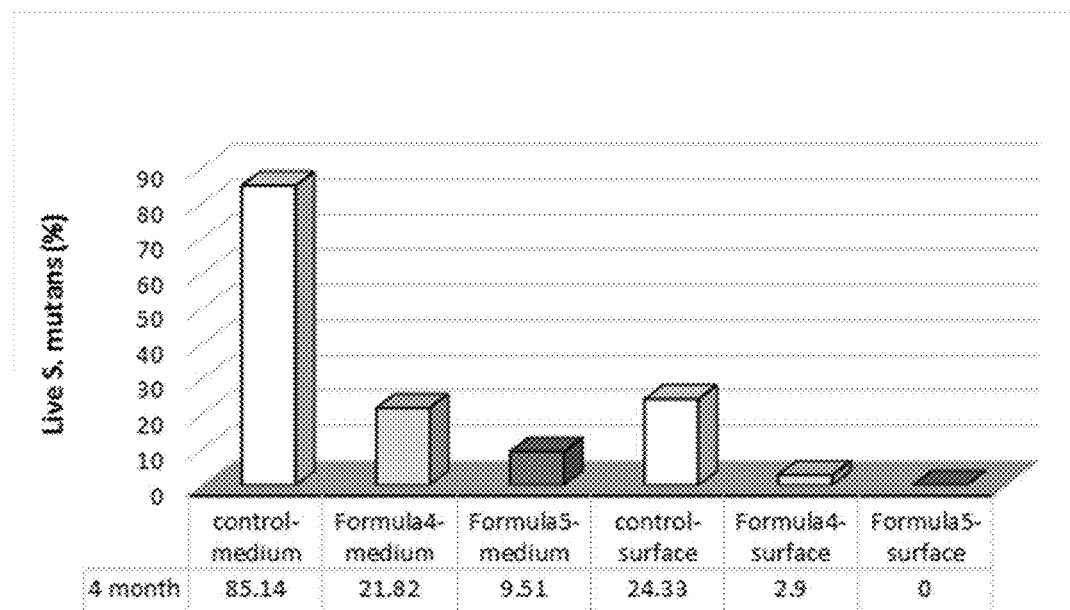
Fig. 6. Long-Term Antimicrobial Activity Testing For *C. albicans*.
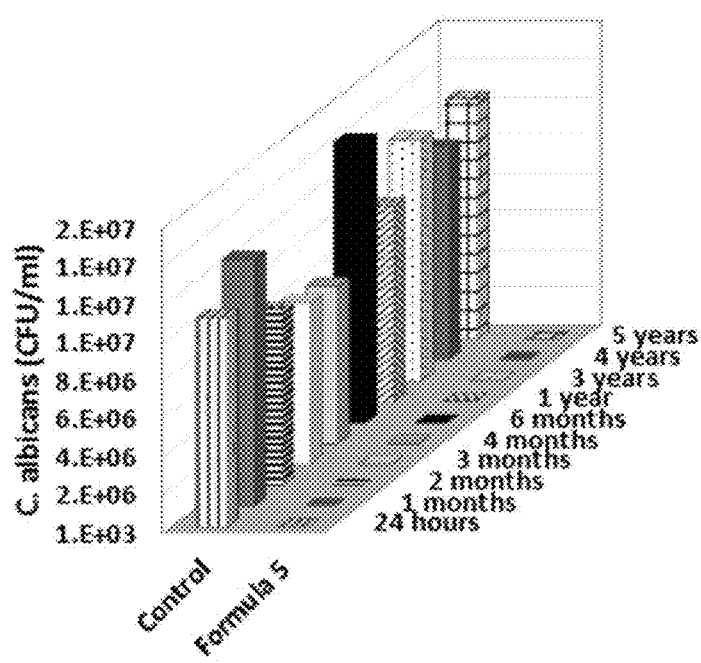

Fig. 7. Long-Term Antimicrobial Activity Testing For *S. mutans*
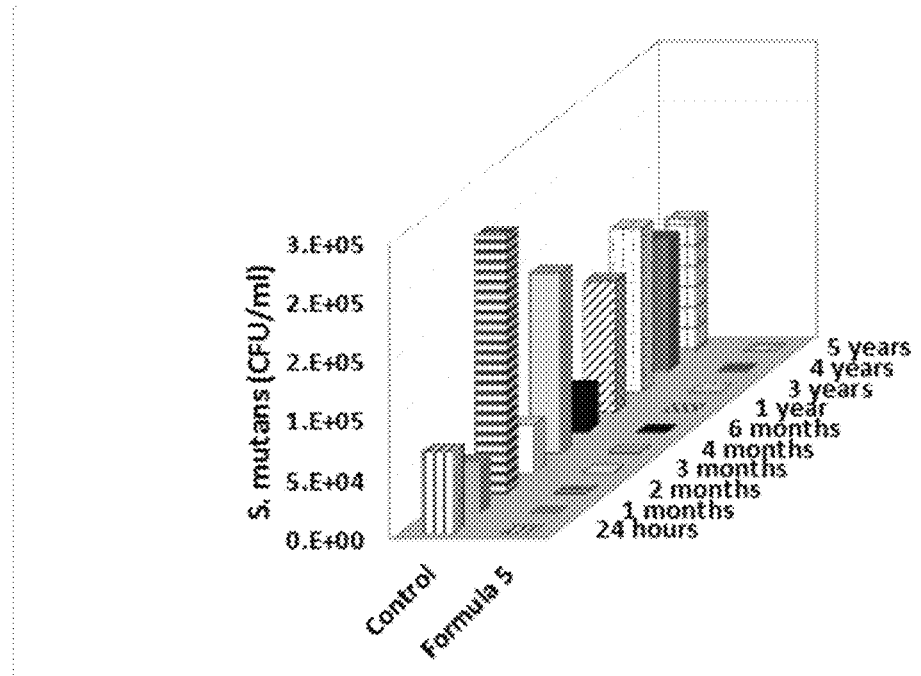
Figure 8. Silver Release Profile Of Extraction in Artificial Saliva
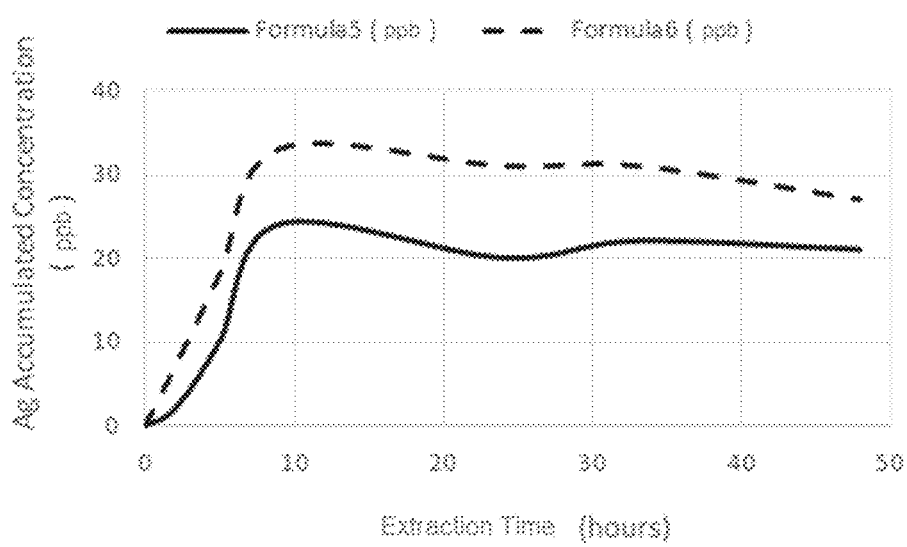

Fig. 9. Long-term Flexural Strength For Antimicrobial Composite Denture Material.
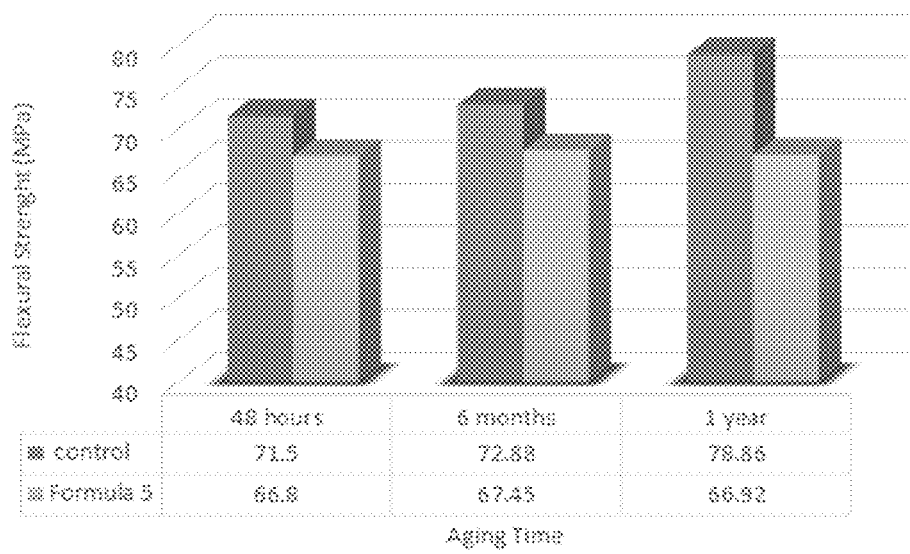
Fig. 10. Long-term Modulus For Antimicrobial Composite Denture Material.
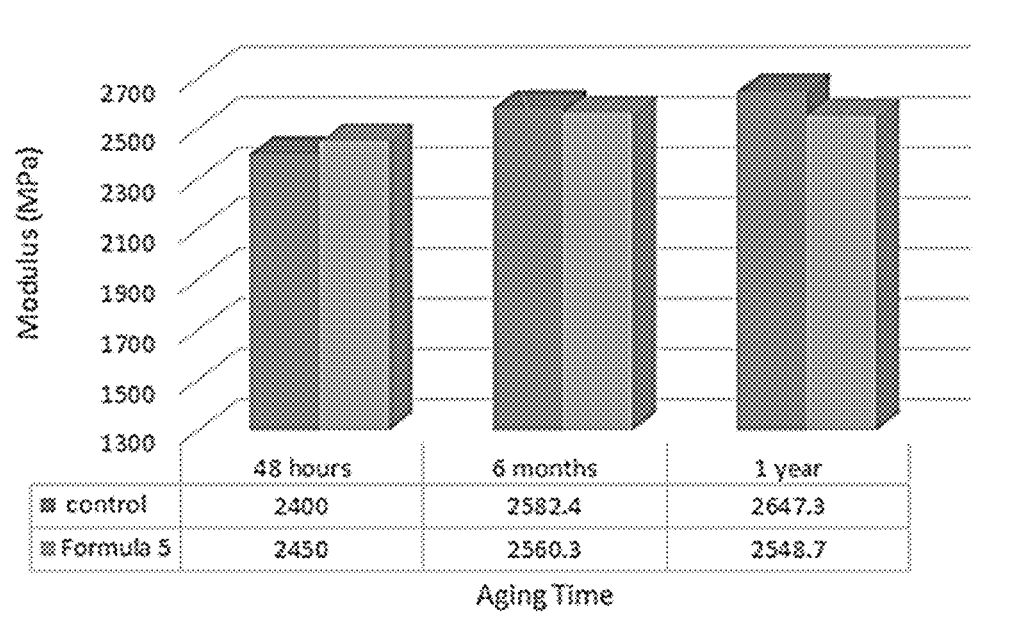

DENTURE MATERIAL HAVING ANTI-MICROBIAL PROPERTIES

RELATED APPLICATIONS

This application is a continuation of U.S. patent application Ser. No. 16/936,059, filed Jul. 22, 2020, which claims the benefit of and priority to U.S. Provisional Patent Application No. 62/876,893, filed Jul. 22, 2019. The entireties of the foregoing applications are incorporated herein by reference.

BACKGROUND

Intraoral devices that reduce bacterial growth and biofilm formation are highly desirable. Approaches for imparting antimicrobial activity have included applying an antimicrobial coating on a surface of an acrylic-based substrate, incorporating silver particles into an acrylic resin, and forming acrylic-based materials that leach small molecule antimicrobial agents, such as chlorhexidine, into the intraoral environment.

U.S. Pat. No. 8,992,223, attempts to reduce colonization and biofilm formation of *Candida albicans* to protect wearers from inflammatory reactions to antigens, toxins and enzymes produced by the microorganism. A polymeric denture substrate is disclosed that elutes an antifungal drug, such as miconazole or chlorhexidine gluconate releasably bound to a polymer, from the polymer over time. The antifungal drug may be washed out from the denture with a quenching solution if no further drug release is needed.

Polymers suitable for use in dental applications may be functionalized to provide antimicrobial activity. Cationic and anionic polymers may be copolymerized with PMMA to form antimicrobial acrylic resins. For example, quaternary ammonium compounds (QAC), such as quaternary ammonium salts (QAS) and quaternary ammonium methacryloxy silicate molecules (QAMS), are known to provide antimicrobial activity when combined in acrylic resins.

A dental composite having particles with antimicrobial activity is disclosed in U.S. Pat. No. 8,889,196. The dental composite comprises up to 90 mass percent amorphous calcium phosphate nanoparticles, a filler, and a resin containing silver nanoparticles and bis(2-methacryloyloxyethyl) dimethyl-ammonium bromide.

SUMMARY

A polymeric composite material is provided that inhibits growth and/or adhesion of common oral bacteria, such as *Streptococcus mutans* (herein, *S. mutans*), and fungus such as *Candida albicans* (herein, *C. albicans*). The antimicrobial polymeric composite material is suitable for medical and dental applications, including medical or dental appliances or devices. Dental devices, such as full or partial arch dentures, dental splints, bridges and the like, comprising the polymeric composite material exhibit long-term antimicrobial activity against colonizing units in ambient and elevated temperatures.

An antimicrobial polymeric composite material is provided that comprises 1) the polymerization product of a composition comprising a polymerizable acrylate monomer, an antimicrobial monomer comprising at least one functional groups comprising an ethylenically unsaturated group, and a quaternary ammonium compound (QAC) group, and 2) an antimicrobial particle component. Monomer components of the compositions may undergo a cold (self-) curing process, or by application of an external energy source, such as irradiation by light or application of heat, or a combination of two or more polymerization processes.

In one embodiment, an antimicrobial polymerizable composition comprises a two-part system wherein a) a first part comprises i. a polymerizable acrylate monomer and ii. an antimicrobial monomer comprising at least two functional groups, an ethylenically unsaturated group and a QAC group, one or both of which comprise a crosslinking group; and iii. co-initiator and b) a second part that comprises i. a powder comprising polymethylmethacrylate (PMMA), ii. antimicrobial particles, and iii. an initiator. In one embodiment, the composition comprises 2 wt % to 20 wt % of an antimicrobial polymerizable silicon-containing monomer comprising a QAC group and 0.01 wt % to 10 wt % of an antimicrobial particle component, based on the total weight of the composition. The second part may comprise greater than 90 wt % of PMMA.

Polymerizable monomers suitable for use herein include known monomer for forming dental acrylic resins, and may comprise one, or two or more ethylenically unsaturated groups, such as acrylate- and methacrylate-based monomers. Monomers may comprise at least one polymerizable acrylic compound selected from monoacrylate, diacrylate, polyacrylate, and methacrylate, such as methyl acrylate (MA), methyl methacrylate (MMA), diurethanedimethacrylate (UDMA), diurethanedimethacrylate (DUDMA), bisphenol A-glycidylmethacrylate (BisGMA), 2,2 bis[4-(methacryloxy ethoxy]phenyl]propane, tricyclodecane dimethanol dimethacrylate, 1,10-decanediol dimethacrylate, ethoxylated trimethylol propane trimethacrylate, triethylene glycol dimethacrylate (TEGMA), 2-methacryloyloxyethyl phosphorylcholine (MPC), ethylene glycol dimethacrylate, diethylene glycol dimethacrylate, and glycerol-dimethacrylate (GDMA), and 1,1,1-trimethylolpropane trimethacrylate (TMPTMA), or 1,4-butanediol dimethacrylate (BDMA), or a combination of one or more, thereof.

An antimicrobial polymerizable monomer may comprise at least one quaternary ammonium (QAC) group and at least one polymerizable functional group having an ethylenically unsaturated group, such as an acrylate or methacrylate. In a one embodiment, the polymerizable monomer comprises a ligand that comprises Si, Ti, P, or Zr. In a further embodiment, a polymerizable monomer may comprise (Si—O), (O—Si—O) and/or (Si—O—Si) bonds. A polymerizable monomer may comprise silane, silicate, siloxane, and/or silanol group. A polymerizable monomer may comprise a quaternary ammonium silane with acrylate functional group, or quaternary ammonium silane with a methacrylate functional group (QASM). A polymerizable monomer may comprise a silsesquioxane-silica hybrid group having a quaternary ammonium group and a polymerizable functional group. An ethylenically unsaturated group may provide polymerization, cross-linking or curing mechanism for the antimicrobial polymerizable composition.

An antimicrobial filler suitable for use herein includes, but is not limited to, antimicrobial particles containing zinc oxide, copper oxide, titanium oxide, silver oxide, silver carbonate, silver zeolite, or silver sodium hydrogen zirconium phosphate, or a combination thereof. In one embodiment, an antimicrobial filler comprises a silver sodium hydrogen zirconium phosphate (SSHZP) compound having approximately 2 wt % to 10 wt % silver metal ion.

To enhance mechanical and esthetic properties, composite material may comprise additives including, fillers known for use in denture composite materials, and colorants. Fillers may include, for example, glass powder, high molecular weight of PMMA beads, and polyvinyl fibers. For example, a PMMA filler may have a molecular weight in the range of 120,000 to 1,500,000 mw.

Antimicrobial composite materials described herein are suitable for use in intraoral dental appliances containing, for example, an acrylic-based substrate, such as full and partial-arch denture bases and orthodontic appliances, such as aligning devices and removable or fixed retainers. Oral devices comprising the antimicrobial composition described herein have demonstrated a long-term reduction in colonization and biofilm formation attributable to microorganism such as *S. mutans* and *C. albicans*. Advantageously, in some embodiments, reduction in colonization and biofilm formation occurs without completely eliminating the detectable growth of the microorganisms in the media, facilitating maintenance of a healthy oral ecology where certain amounts and types of microorganisms found in the mouth may be helpful in preventing disease. Moreover, the composite materials provided herein maintain strength properties, and have shown a slow sustained release rate of antimicrobial agents, such as silver, from the composite material.

In one embodiment, a denture base comprises antimicrobial polymeric composite material that is the polymerization product of a composition comprising a polymerizable acrylate monomer, 3 wt % to 6 wt % of an antimicrobial polymerizable quaternary ammonium silane monomer with methacrylate functionality, an antimicrobial particle component comprising greater than 0.1 wt % SSHZP, and a PMMA filler. In this embodiment, the dental composite material provides greater than 99% reduction in *S. mutans, S. mitis, L. casei* and/or *P. gingivalis* when tested according to a contact-killing test provided herein.

In another embodiment, an antimicrobial denture composite material comprising at least 80 wt % of an acrylic resin, between 3 wt % to 6 wt % of an antimicrobial polymerizable quaternary ammonium silane or siloxane monomer, and about 0.5 wt % and 2 wt % silver sodium hydrogen zirconium phosphate (SSHZP), has at least 99.9% reduction in *S. mutans* for at least 3 months, and at least 99.9% reduction in *C. albicans* for at least 3 months, when tested according to the real-time antimicrobial tests provided herein. In another embodiment, an antimicrobial denture composite material comprising at least 80 wt % of an acrylic resin, between about 3 wt % and 6 wt % of an antimicrobial polymerizable quaternary ammonium silane monomer and at least 1.5 wt % SSHZP, has at least a 99.9% reduction in *S. mutans* for 12 months or longer, and greater than 99.9% reduction in *C. albicans* for at least 12 months when tested according to an accelerated antimicrobial test provided herein.

BRIEF DESCRIPTION OF THE DRAWINGS

FIG. 1. A graphical representation of antimicrobial activity testing for *S. mutans*.

FIG. 2. A graphical representation of antimicrobial activity testing for *C. albicans*.

FIG. 3. A graphical representation of antimicrobial activity testing for *C. albicans*.

FIG. 4. A graphical representation of antimicrobial activity testing for *S. mutans*

FIG. 5. A graphical representation of bacterial viability of *S. mutans* of an aged sample (four months).

FIG. 6. A graphical representation of antimicrobial activity testing for *C. albicans*.

FIG. 7. A graphical representation of antimicrobial activity testing for *S. mutans*.

FIG. 8. A graphical representation of silver release from an antimicrobial composite material.

FIG. 9. A graphical representation of flexural strength for antimicrobial composite denture material.

FIG. 10. A graphical representation of modulus for antimicrobial composite denture material.

DETAILED DESCRIPTION

As used throughout and herein, the terms "a", "an" and "the" include singular and plural references unless indicated otherwise. The term 'antimicrobial' refers to an inhibiting effect on the growth and/or adhesion of bacteria and/or fungus according to the tests provided herein. The term "alkyl" is characterized by a linear, branched aliphatic or cyclic hydrocarbon having from 1 to about 20 carbon atoms, including but not limited to, methyl, ethyl, n-propyl, iso-propyl, n-butyl, iso-butyl, or t-butyl, which, optionally, may be substituted or unsubstituted. The term "alkylenyl" refers to divalent analog of a linear, branched or cyclic hydrocarbon group, which, optionally, may be substituted or unsubstituted. The term "alkenyl" as used herein refers to an unsaturated linear or branched hydrocarbon having from 2 to about 30 carbon atoms, such as, ethenyl or vinyl, allyl, propenyl, butenyl, pentenyl, hexenyl, octenyl, or a cycloalkenyl, such as cyclopentenyl. The term aryl "refers" to an aromatic ring, including bicyclic, tricyclic, or other multi-cyclic aromatic ring systems that, optionally, may be substituted or unsubstituted. The term "halide" includes, for example, fluorine, bromine, chlorine or iodine. The term "optionally substituted" refers to replacement of one or more hydrogens, such as from one to four hydrogens. with a suitable substituent which, independently, may include, but is not limited to, hydroxyl, nitro, amino, imino, cyano, thio, sulfonyl, halo, carboxyl, alkyl, aryl, alkenyl, alkylenyl, cycloalkyl, haloalkyl, alkylamino, arylalkyl, alkylyl, and the like, which in turn, may also be substituted by a suitable substituent as described above.

A polymeric composite material is provided that inhibits growth and/or adhesion of common oral microorganisms, such as *S. mutans* and *C. albicans*. The composite material is suitable for use in forming appliances for oral applications, including oral devices having substrates that contact the gums or palate of a patient, such as the base of full or partial arch dentures, or dental splints, bridges, and the like. Antimicrobial composite materials used to form a substrate that contact the gums or palate of a patient when a dental appliance is fitted in the mouth of a patient material exhibit long-term activity against microbial colonizing units at body temperature (approximately 37° C.).

An antimicrobial polymeric composite material is provided that comprises the polymerization product of a composition comprising a polymerizable acrylate monomer, an antimicrobial polymerizable monomer comprising at least two functional groups that comprises an ethylenically unsaturated group and a QAC group, and an antimicrobial particle component. Compositions for forming the antimicrobial composite may comprise a one-part, or two-part polymer system, optionally, polymerizable by cold (self-) curing, or by application of external energy source such as irradiation by light or application of heat, or a combination of two or more polymerization processes.

In one embodiment, an antimicrobial polymerizable composition comprises a two-part system wherein a) a first part comprises, i. a polymerizable acrylate monomer and ii. an antimicrobial polymerizable monomer comprising at least two functional groups that comprises an ethylenically unsaturated group and a QAC group; and b) a second part comprises i. polymethylmethacrylate (PMMA) powder, ii. an antimicrobial particle component, iii. optionally, a filler and iv. optionally, a colorant. The weight ratio of the first part (liquid) and the second (powder) part may be in a range of about 1 to 2 parts liquid component to about 1 to 3 parts powder, such as 2 parts liquid component to 3 parts powder component.

A polymerizable monomer suitable for use herein comprises one, two or more ethylenically unsaturated groups, and may comprise at least one polymerizable acrylic-based compound comprising a monoacrylate, diacrylate, polyacrylate, or methacrylate group. The composition may comprise at least one polymerizable acrylic compound, including, but not limited to, methyl acrylate (MA), methyl methacrylate (MMA), diurethanedimethacrylate (UDMA), diurethanedimethacrylate (DUDMA), bisphenol A-glycidylmethacrylate (BisGMA), 2,2 bis[4-(methacryloxy ethoxy]phenyl]propane, tricyclodecane dimethanol dimethacrylate, 1,10-decanediol dimethacrylate, ethoxylated trimethylol propane trimethacrylate, triethylene glycol dimethacrylate (TEGMA), 2-methacryloyloxyethyl phosphorylcholine (MPC), ethylene glycol dimethacrylate, diethylene glycol dimethacrylate, and glycerol-dimethacrylate (GDMA), and 1,1,1-trimethylolpropane trimethacrylate (TMPTMA), or 1,4-butanediol dimethacrylate, or a combination of one or more monomers, thereof. In some embodiments, an antimicrobial polymerizable composition comprises at least one polymerizable monomer, such as an polymerizable acrylic-based compound, in an amount of about 25 wt % to about 75 wt %, or about 30 wt % to 70 wt %, or 30 wt % to 60 wt %, based on the total weight of the antimicrobial polymerizable composition.

An antimicrobial polymerizable monomer suitable for use herein comprises at least one quaternary ammonium compound (QAC), and at least one polymerizable ethylenically unsaturated group, such as, an acrylate or methacrylate, or combination thereof. The antimicrobial polymerizable monomer may comprise a ligand that comprises, for example, Si, Ti, P, or Zr. An polymerizable, antimicrobial compound may comprise one or more of (Si—O), (O—Si—O) and/or (Si—O—Si) bonds in addition to the ethylenically unsaturated group and quaternary ammonium group. A polymerizable monomer may comprise silane, silicate, siloxane, and/or silanol group. An antimicrobial polymerizable monomer may comprise a quaternary ammonium silane having an acrylate or methacrylate group (QASM), such as quaternary ammonium methacryloxy silicate (QAMS), for example, as described in U.S. Pat. No. 10,159,630, issued Dec. 25, 2018, the subject matter of which is hereby incorporated herein by reference in its entirety. A polymerizable monomer may comprise a silsesquioxane-silica having dual functionality, for example, as described for example in U.S. Pat. No. 10,189,954, issued Jan. 29, 2019, the subject matter of which is, hereby, incorporated herein by reference in its entirety.

An antimicrobial polymerizable silicon-containing compound may be formed by reacting i) a compound having silane functionality; ii) a compound having silane functionality and an antimicrobial quaternary ammonium group; and iii) a compound having silane functionality and an ethylenically unsaturated group. The silane compounds may comprise alkoxysilane, such as a mono-, di-, tri- or tetra alkoxysilane (e.g., tetraethyl orthosilicate, or TEOS), or a combination thereof. In one embodiment, a method for making an antimicrobial monomer comprises co-condensing a tetralkoxysilane with a trialkoxysilane having crosslinking functionality, and a second trialkoxysilane having antimicrobial activity as described in U.S. Pat. Nos. 10,159,630 and 10,189,954. For example, a curable antimicrobial quaternary ammonium silane may be prepared from the reaction of tetraethoxy silane, methacryloxy propyltrimethoxy silane, and octadecyldimethyl trimethoxysilyl-propyl ammonium chloride.

An antimicrobial compound may comprise a quaternary ammonium silane-functionalized compound having from one to three ethylenically unsaturated groups, such as an acrylate or methacrylate functional group, from one to three quaternary ammonium (QAC) groups, and (Si—O), (O—Si—O) and/or (Si—O—Si) bonds.

In one embodiment, an antimicrobial polymerizable monomer may comprise at least one compound of Formula I:

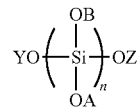

where n is 1 through 5, and wherein A, B, Y and Z, are each independently selected from H, $(C_1$ to $C_8)$alkyl, Formula II

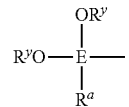

and Formula III

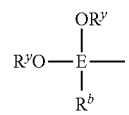

where E is Si or Ti; where $R^a$ is selected from a polymerizable Group comprising an ethylenically unsaturated group selected from acrylate, methacrylate, $(C_2$ to $C_8)$alkenyl, glycidyloxy, epoxy, sulfonate, carboxylate, ester, amino, acrylamide, methacrylamide, isocyanato, amino acid, and nucleic acid; $R^y$ is independently H and $(C_1$ to $C_8)$alkyl; and where $R^b$ is selected from a quaternary ammonium, such as

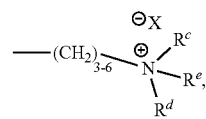

such as

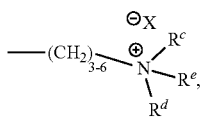

where $R^c$ is selected from $C_1$ to $C_2$ alkyl; $R^d$ is selected from $C_1$ to $C_2$ alkyl or phenyl; $R^e$ is selected from $C_6$ to $C_{22}$ alkyl, and $X^-$ is an anion selected from chloride, bromide, fluoride, iodide, sulfonate and acetate. In some embodiments, at least one A, B, Y or Z group comprises Formula II., and at least one A, B, Y or Z group comprises Formula III. In a further embodiment, at least two of A, B, Y and Z comprise Formula II and at least two of A, B, Y and Z comprise Formula III.

In some embodiments of Formula III, $R^b$ may be —($C_3$-$C_6$ alkylenyl)-(dimethyl)-($C_6$-$C_{22}$alkyl) quaternary ammonium chloride, such as —($C_3$-$C_6$ alkylenyl)-(dimethyl)-($C_{18}$alkyl) quaternary ammonium chloride, or —($C_3$-$C_6$ alkylenyl)-(methyl)-(phenyl)-($C_6$-$C_{22}$alkyl) quaternary ammonium chloride. Commercially available monomers may be obtained, for example, from Aegis (e.g., Aegis® 5700 or 5772).

In one embodiment, the antimicrobial polymerizable monomer comprises a quaternary ammonium silane having methacrylate functionality that may comprise the following structure

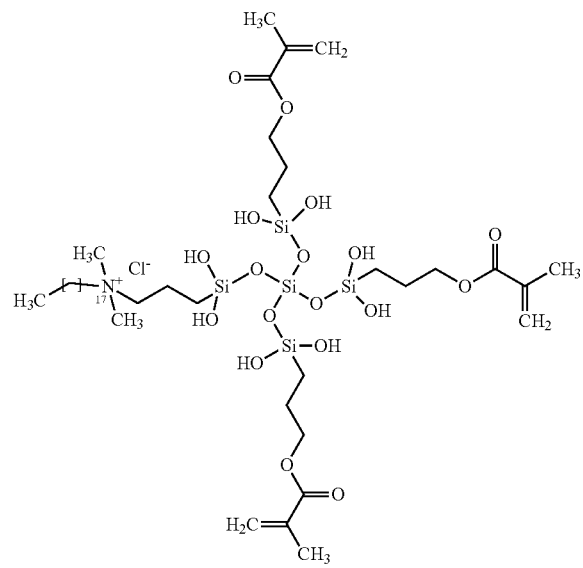

In some embodiments, the composition comprises from 2 wt % to 20 wt %, or 2 wt % to 15 wt %, or 2 wt % to 10 wt %, or 2 wt % to 8 wt %, or 2 wt % to 6 wt %, or 2 wt % to 5 wt %, or 3 wt % to 15 wt %, or 3 wt % to 10 wt %, or 3 wt % to 8 wt %, or 3 wt % to 6 wt %, or 3 wt % to 5 wt %, of an antimicrobial polymerizable monomer, such as antimicrobial polymerizable quaternary ammonium silane having methacrylate functionality, based on the total weight of the polymerizable composition. Ten weight percent to 70 wt % of the antimicrobial polymerizable quaternary ammonium monomer may be premixed with a diluent such as a solvent, including ethanol, or a polymerizable acrylate monomer such as MMA, GDMA, TEGMA or HEMA ((hydroxyethyl) methacrylate).

A dental composite material provided herein comprises an antimicrobial particle component. In some embodiments, antimicrobial particles comprise silver, such as silver oxide, silver carbonate, silver zeolite, or zinc oxide, copper oxide or titanium oxide. Antimicrobial particles may include carbon-based, ceramic, metal, and polymeric nanoparticles acting as a substrate to an antimicrobial agent, such as silver or silver calcium phosphate. In one embodiment, antimicrobial particles comprise a silver-emitting ceramic, such as a silver sodium hydrogen zirconium phosphate (SSHZP) compound containing between 3 wt % and 10 wt % silver metal ion, based on the weight of the SSHZP compound (e.g., SSHZP sold under the trade name, SelectedSilver® Zr2K, by Milliken & Company).

Antimicrobial particles suitable for use herein include those having a high surface area to increase efficiency in reducing bacterial and fungal growth. Particles may have a size of approximately between 1 nm and 5 µm, or between 1 nm and 3 µm, or between 1 nm and 1 µm. Particle shapes suitable for use herein may be symmetrical or asymmetrical, such as spherical, diamond, octagonal, rhombohedral, non-spherical, or irregularly shaped particles, and the like. In some embodiments, the antimicrobial particle component may be present in an amount from 0.1 wt % to 10 wt %, 0.2 wt % to 10 wt %, 0.25 wt % to 10 wt %, 0.5 wt % to 10 wt %, 1 wt % to 10 wt %, 1.5 wt % to 10 wt %, 2 wt % to 10 wt %, 2.5 wt % to 10 wt %, 3 wt % to 10 wt %, 0.1 wt % to 6 wt %, 0.25 wt % to 6 wt %, 0.5 wt % to 6 wt %, 1 wt % to 6 wt %, 1.5 wt % to 6 wt %, 2 wt % to 6 wt %, 2.5 wt % to 6 wt %, 0.1 wt % to 4 wt %, 0.25 wt % to 4 wt/o, 0.5 wt % to 4 wt %, 0.5 wt % to 4 wt %, 1 wt % to 4 wt %, 1.5 wt % to 4 wt %, and 2 wt % to 4 wt %, based on the total weight of the polymerizable composition. In some embodiments, an antimicrobial composition may comprise 3 wt % to 10 wt % of a zinc oxide, or 0.1 wt % to 10 wt % of silver, silver oxide or a combination thereof, based on the total weight of the antimicrobial polymerizable composition.

In addition to antimicrobial fillers, composite material may comprise other fillers known to enhance mechanical and esthetic properties in denture composite materials. Fillers may comprise an inorganic filler, an organic filler, or a combination thereof. Inorganic fillers may comprise silica, titanium dioxide, iron oxide, and silicon nitride, and a combination thereof. Glass fillers may comprise glass powder, including aluminum-based glass, borosilicate glass, strontium borosilicate, lithium silicate, lithium alumina silicate, silanized barium boron aluminosilicate, and silanized fluoride barium aluminosilicate, and a combination thereof. One or more fillers, including antimicrobial fillers may be added in an amount of up to 30 wt %, or 40 wt %, or 50 wt %, or 60 wt %, or 70 wt %, such as between 30 wt % and 60 wt %, based on the total weight of the polymerizable composition.

Organic fillers include pre-polymerized organic polymeric fillers, such as poly(methyl/ethyl methacrylate), poly(methyl/butyl methacrylate), or a combination thereof, or PMMA, such as high molecular weight PMMA beads. PMMA powder, for example, may be added to enhance physical properties and/or reduce shrinkage. Fibers, such as polyvinyl fiber, may be added in an amount up to about 2 wt % of the polymerizable composition. Fibers may comprise nylon, polyamide, polyethylene, polypropylene or polyacrylonitrile, or a combination thereof. Pre-polymerized organic materials, such as PMMA, suitable for use herein include polymers having a molecular weight between 20,000 and 2,000,000, or between 90,000 and 1,000,000, or between 150,000 and 750,000, or between 200,000 and 550,000.

Optionally, PMMA powder comprises a bead size between 10 μm and 1000 μm, or between 10 μm and 200 μm, or between 20 μm and 150 μm, or between 25 μm and 100 μm.

An antimicrobial composite material may comprise additional additives including initiators and co-initiators, stabilizers, opacifiers, colorants, and the like. The antimicrobial composition may comprise up to 5 wt % of an opacifier, such as zinc oxide, zirconium oxide, aluminum oxide, or titanium oxide, or a combination thereof. An antimicrobial composition may further comprise an initiator or initiator system. In a heat curable, two-part composition, the second part, or powder part, may comprises an initiator, such as benzoyl peroxide (BPO). A cold curable, two-part composition may comprises an initiator system having an amine in the first part (liquid) of the antimicrobial composite material, and BPO in the second part (powder) of the composite material. The amine may comprise an aromatic amine, N,N-dimethyl-p-toluidine (DMPT), N, N-dihydroxyethyl-para-toluidine, or a combination thereof. A composition that is light curable may comprise a photoinitiator system, such as camphorquinone (CQ), and ethyl 4-(dimethylamino)benzoate (EDMAB), TPO (monoacrylphosphine oxide), Ir819 (bisacrylphosphine oxide), 2,4,6-trimethylbenzoyldiphenylphosphine oxide, or methylbenzoin. The initiator may be present in an amount of at least 0.05 wt % to 2 wt %, based on the weight of the polymerizable composite material. An antimicrobial composition may further comprise an inhibitor or a stabilizer such as butylated hydroxytoluene (BHT), hydroquinone (HQ), methyl ether of hydroquinone (MEHQ) or butylated hydroxyanisole (BHA) in an effective amount. In some embodiments, the inhibitor may be present in an amount of 0.05 wt % to 1 wt %, based on the weight of the polymerizable composite material.

In one embodiment, a polymerizable composition comprises a two-part system in which a) a first part comprising a liquid component comprises i. a polymerizable acrylate monomer, such as MMA, and ii. a polymerizable QAMS monomer; and b) a second part comprising a powder component comprises i. a polymethylmethacrylate, (PMMA) powder, ii. an antimicrobial SSHZP particle component, iii. optionally, a filler and iv. optionally, a colorant. The polymerizable composition may comprise 1 wt % to 20 wt % of a polymerizable QAMS monomer, and 0.01 wt % to 10 wt % of an antimicrobial SSHZP particle component, based on the total weight of the composition. The second part (powder component) may comprise 80 wt % to 97 wt % of PMMA powder, and 1 wt % to 8 wt % of other fillers, based on the weight of the second part. The composition may further comprise an initiator system or stabilizer, or fibers in an amount of 0.1 wt % to 3 wt % based on the total weight of the composition.

In some embodiments of a two-part composite system, the polymerizable acrylate monomer, such as MMA, comprises at least 70 wt %, or at least 80 wt %, or at least 85 wt %, such as between 75 wt % and 95 wt %, based on the weight of the first (liquid) component. In one embodiment of a two-part dental composite system, a first liquid component comprises MMA and BDMA. In a further embodiment, the polymerizable acrylate monomer comprises at least 70 wt %, such as between 75 wt % and 95 wt %, of MMA, based on the weight of the first component, and at least 4 wt %, or at least 5 wt %, or at least 10 wt %, of a crosslinking monomer, such as BDMA, an antimicrobial polymerizable monomer, such as QAMS, or a combination of a crosslinking monomer such as BDMA and an antimicrobial polymerizable monomer.

A method for making an antimicrobial polymerizable composition may comprise preparing a liquid part of a two-part system by forming a homogeneous liquid resin mixture comprising an antimicrobial polymerizable QAMS monomer, at least one polymerizable acrylate monomer, an initiator and a stabilizer. The components may be mixed by mechanical stirring at room temperature. The liquid part may be mixed with a powder part comprising a well-dispersed mixture comprising an antimicrobial filler, other fillers and/or fibers, a polymer powder such as PMMA. The liquid part may be mixed with the powder part at, for example, a 2:1 to 1:3 mass ratio of liquid to powder. The two-part mixtures may be stirred to ensure complete wetting of the powder. The composite mixture may be poured into molds and allowed to harden or cure at ambient conditions, or heated to polymerize, with or without pressure.

In one embodiment of a single component system, an antimicrobial polymerizable composition comprises polymerizable acrylate monomer, an antimicrobial polymerizable quaternary ammonium silane monomer, an antimicrobial particle, a photoinitiator system, a filler and a colorant. In some embodiments, the composition comprises 50 wt % to 75 wt %, of a polymerizable acrylate monomer, 2 wt % to 20 wt % of an antimicrobial polymerizable quaternary ammonium silane monomer, 0.01 wt % to 10 wt % of the antimicrobial particle, 10 wt % to 30 wt % of other fillers, and a photoinitiator system, based on the total weight of the dental composite material.

In a further embodiment, an antimicrobial polymerizable quaternary ammonium silane monomer, such as QAMS, and an antimicrobial particle component, such as SSHZP, may be incorporated into known, or commercially available, denture material systems. For example, an antimicrobial monomer, such as QAMS, may be added to a liquid portion of a commercially available, two-component powder-liquid (PMMA/MMA) system, and an antimicrobial filler may be added to the powder portion of the two-component system prior to mixing the first and second components. Two-component denture polymer systems suitable for use herein include commercially available systems under the trade name, e.g., Ivoclar ProBase Cold/Hot denture, Excel Denture or ThermoDent, In a further embodiment, an antimicrobial monomer, such as a polymerizable QAMS monomer, and antimicrobial filler, such as SSHZP, may be added to a commercially available single component polymer system, such as a three-dimensional printable bis-GMA polymer system (e.g., available under the name NextDent, Dentca Denture). Both the antimicrobial polymerizable monomer and the antimicrobial filler may be mixed with the single-component polymer product. Light curable systems suitable for use herein may include denture materials that are commercially available under the tradenames Primobase (Primotec USA) and Triad Denture Base (Dentsply).

Composite denture materials are disclosed that reduce or slow the release of antimicrobial agents or filler material from the polymer composite over time, thereby increasing the long-term effectiveness of the denture material in reducing microbial growth. Upon exposure to saliva, antimicrobial agents, such as silver ions, incorporated into denture polymer materials may be released from some denture polymers over time. Release may occur by an ion exchange between silver ions in the denture and ions such as sodium, potassium, calcium and/or magnesium in the saliva, or chelation by protein molecules in saliva, or detachment of silver-containing particles from denture surfaces. Denture composite materials are disclosed that are effective in reducing release of antimicrobial agents, therefore, maintain effective antimicrobial activity over long-term contact with saliva. In some embodiments, disclosed materials have at least a 25% slower release rate of silver compared to conventional dental polymers in which silver emitting zirconia particles are added, when tested up to 48 hours by the methods described herein. In some embodiments, a dental composite material is provided that releases fewer than 25 ppb silver when tested at 48 hours according to the methods described herein.

In one embodiment, a quaternary ammonium methacrylate silicate (QAMS)—containing acrylic resin composite material that is the polymerization product of a composition comprising a polymerizable acrylate monomer, 3 wt % to 6 wt % of an antimicrobial polymerizable quaternary ammonium silane having an ethylenically unsaturated group, greater than 0.1 wt % silver sodium hydrogen zirconium phosphate (SSHZP), provides greater than 99% reduction in *S. mutans, L. casei, P. gingivalis*, and/or *C. albicans*, when tested according to a contact-killing test. In another embodiment, the antimicrobial denture composite material comprising greater than 0.2 wt % silver sodium hydrogen zirconium phosphate (SSHZP) the material has at least 99.9% reduction in *S. mutans*, for at least 3 months, and at least 99.9% reduction in *C. albicans* for at least 3 months, when tested according to a contact-killing test provided herein.

In further embodiment, a QAMS-containing acrylic resin composite material made from a polymerizable composition comprising acrylate monomer, 3 wt % to 6 wt % of an antimicrobial polymerizable quaternary ammonium silane monomer, and between 0.25 wt % and 2 wt %, of silver sodium hydrogen zirconium phosphate (SSHZP), provides at least 99.9% reduction in *S. mutans* for at least 3 months, and at least 99% reduction in *C. albicans* for at least 1 month, when tested according to the real time long term antimicrobial activity test provided herein. In a further embodiment, the composite material having greater than 0.5 wt % silver sodium hydrogen zirconium phosphate (SSHZP), may have greater than 99.9% reduction in *S. mutans* for at least 3 months, and greater than 99.9% reduction in *C. albicans* for at least 3 months, when tested according to the real time long term antimicrobial activity test. The composite material provided herein having greater than 1 wt % silver sodium hydrogen zirconium phosphate (SSHZP), may have greater than 99.9% reduction in *S. mutans* for at least 6 months, and greater than 99.9% reduction in *C. albicans* for at least 4 months, may be achieved when tested according to the real time long term antimicrobial activity test. A composite material having greater than 1.5 wt % silver sodium hydrogen zirconium phosphate (SSHZP) may have greater than 99.9% reduction in *S. mutans* for at least 12 months (when tested according to the accelerated aging test method described herein), and greater than 99.9% reduction in *C. albicans* for up to 4 months, when tested according to the real time long term antimicrobial activity test.

A dental composite material may be formed that resists denture biofilm formation. In one embodiment, a denture composite material made from a polymerizable composition comprising 3 wt % to 4 wt % of antimicrobial polymerizable quaternary ammonium silane monomer and at least 1 wt % silver sodium hydrogen zirconium phosphate (SSHZP), has greater than 99% reduction in *S. mutans* biofilm formation on the denture material surface after 24 hours, and bacteria survival rate in media of less than 20%, when tested according to the drip flow biofilm reactor, followed by LIVE/DEAD® BacLight™ Bacterial Viability staining test.

Test Methods

Strength Testing

The flexural strength and flexural modulus of denture materials were evaluated according to the specification outlined in ISO-20795-1. Accordingly, two acrylic plates (65 mm×40 mm×5 mm) were fabricated for each sample. Each plate was sectioned lengthwise into three strips using a precision cutting machine (Isomet High Speed Pro, Buchler, Lake Bluff, IL, USA) under water cooling to prevent overheating. The strips were then ground to the required length, width, and height of 64 mm×10 mm×3.3 mm, with an automatic grinding and polishing unit (RotoPOl-11, Struers) under water cooling, using metallographic grinding paper (MD Piano Metal) with a grain size of approximately 30 μm, 18 μm and 15 μm. Specimens free of porosity were selected for flexural testing (n=6). The resulting bar width and height were recorded, and the specimens were stored in deionized water at 37° C.±1° C. for 50 hours±2 hours, prior to strength testing. The specimens were retrieved from water storage, and the flat surface was symmetrically placed on the supports of the flexural test rig immersed in the water bath. The specimens were allowed to come to equilibrium with the water bath temperature. An increased loading force was applied through a universal testing machine (Model 5564, Instron Corp. USA), at a constant displacement rate of 5±1 mm/min until the specimen broke. The flexural strength (□, in MPa) was calculated from the equation:

$$\sigma = Fl/2bh^2$$

where F is maximum load (N) exerted on the specimen, l is the distance (mm) between the supports, b is the specimen width (mm) and h the specimen height (mm) prior to water storage. The flexural modulus (E, in MPa) was calculated from the equation:

$$E = F_1 l^2 / 4bh^2 d$$

where $F_1$ is the load (N) at a point in the straight line portion of the load/deflection curve, d is the deflection (mm) at load $F_1$.

Water Sorption and Solubility

Water sorption and solubility were determined substantially according to the ISO specification for denture base polymers (ISO-20795-1), except that the specimen dimensions used herein measured 50 mm±0.1 mm diameter, 0.5 mm±0.1 mm thick, and the top and bottom surfaces were flat. After polymerization, specimens (n=5) were stored at 37° C. in desiccator containing freshly dried silica gel. The specimens were repeatedly weighed in an electronic analytical balance after 23±1 hours until a constant mass (m1) was obtained. Thereafter, the diameter and the thickness of the specimens were measured for determining the volume (V) of each specimen. The specimens were then immersed in deionized water at 37° C. for 7 days±2 hours. After this time, the discs were removed from the water with polymer coated tweezers, wiped with a clean, dry towel until free from visible moisture, waved in the air for 15 seconds, and then, the mass was recorded as m2. The specimens were reconditioned to a dry, constant mass (m3) following the same protocol as for conditioning the specimens prior to water immersion. Water sorption ($W_{sp}$, μg/mm³) and water solubility ($W_{sb}$, μg/mm³) were calculated using the following equations:

$$Wsp = \frac{m2 - m3}{V\cos\alpha + \cos\beta = 2\cos\frac{1}{2}(\alpha + \beta)\cos\frac{1}{2}(\alpha - \beta)}$$

$$Wsb = \frac{m1 - m3}{V}.$$

Residual Methyl Methacrylate (MMA) Monomer

Residual methyl methacrylate monomer was analyzed according to the ISO specification for denture base polymers (ISO20795-1). Solvent extraction was used to extract the methyl methacrylate (MMA) monomer from polymerized denture base material followed by chromatographic analysis (HPLC method). Three specimens (50 mm diameter and 3.0 mm±0.1 mm thick) from separate batches of the same formula were fabricated and kept in the dark in a laboratory environment for 24 hours±5 hours prior to grinding. The material was wet-grinded equally on both sides of the specimen disc, using metallographic grinding papers to a thickness of 2.0 mm±0.1 mm. The specimens were stored in the dark in a lab environment for 24 hours±1 hours prior to extraction of the monomer.

Three sample solutions were analyzed from each test specimen for a total of nine sample solutions. A 650 mg sample of each specimen disc was weighed, broken into small pieces, placed in a one-mark 10 ml volumetric glass flask with analytical balance, and recorded. Acetone solution was added until the total volume was 10 ml and then it was stirred for 72 hours±2 hours at room temperature (T).

The dissolved polymer was precipitated by using a volumetric pipette to transfer a 2 ml aliquot of each previously prepared sample solution to separate one-mark closable 10 ml volumetric glass flasks. Methanol solution was added until the total volume was 10 ml. Approximately 5 ml of the polymer/monomer containing slurry was transferred from each of the 10 ml flasks to separate closable glass centrifugation tubes and centrifuged at 3000×$g_n$ m/s$^2$ for 15 minutes. After centrifuging, approximately 3 ml aliquot of each centrifuged solution was transfer to separate closable glass tubes.

HPLC Method for Determination of MMA Content

Calibration solution preparation was prepared as follows. 30 mg of MMA was transferred into a 100 ml volumetric flask, and a mixture solution of acetone to methanol of 1:4 was added until the total volume was 100 ml, which was used as stock solution. From the stock solution, a series of dilutions was made to obtain standard solutions with concentrations of 30 µg/ml, 75 µg/ml, 150 µg/ml, 225 µg/ml, and 300 µg/ml. Peaks from HPLC chromatograms were evaluated to determine the retention time and the peak height of MMA by integration using HPLC, Agilent 1200 with UV detector. The percentage of MMA residual monomer was calculated with the following equation (where m is mass):

Residual monomer(% mass)=$m_{MMA}/m_{sample}$×100.

Microbiology Test Methods
Antimicrobial Test—ASTM E2180 (2017)

Standard test methods were performed for determining antimicrobial activity of incorporated antimicrobial agent(s) in polymeric or hydrophobic material (ASTM E2180-07 (2017)).

*Streptococcus mutans* (*S. mutans*) (ATCC 25175) and *Streptococcus mitis* (*S. mitis*) (ATCC 49459) were cultured in tryptic soy broth (TSB)/brain heart infusion (BHI) broth. *Candida albicans* (*C. albicans*) (ATCC 14053) was cultured in Sabouraud Dextrose (SabDex) broth. *Lactobacillus casei* (*L. casei*) (ATCC 393) was cultured in Lactobacilli MRS Agar. *Porphyromonas gingivalis* (*P. gingivalis*) (ATCC 33277) was cultured with Brucella Blood agar.

Overnight cultures were used to grow a 24 hour pseudo-biofilm on treated and control samples. Sample discs were prepared having 30 mm diameter and 1.0 mm in thickness. A thin layer of inoculated agar slurry (about 0.5 ml to 1.0 ml) was pipetted onto discs of control and treated materials (samples were prepared at least in triplicate).

After 24 hours±2 hours contact time, surviving microorganisms were recovered by eluting the agar slurry inoculum from the substrate of the sample discs into neutralizing broth. Serial dilutions were made from the neutralizing broth, then poured or spread onto plates and incubated 48 hours±2 hours, at 37° C. Colonies from each dilution series were counted and recorded. Percent reduction from treated versus untreated (control) samples was calculated.

The geometric mean of the number of organisms recovered from the triplicate incubation period control and incubation period treated samples was calculated by the following equation:

Geometric mean=($Log_{10}X_1$+$Log_{10}X_2$+$Log_{10}X_3$)/3

Percent Reduction(% reduction)=$(a-b)/a$×100 wherein, a=the antilog of the geometric mean of organisms recovered from the incubation period control samples, and b=the antilog of the geometric mean of the number of organisms recovered from the incubation test samples.

Drip Flow Biofilm Growth Study

Biofilm formation was simulated under continuous flow conditions in a modified drip-flow reactor for 20 hours followed the ASTM standard (ASTM-E2647). For simulating *S. mutans* (ATCC 25175) biofilm formation under dynamic conditions, a modification of a commercially available drip-flow reactor (DFR 110-4PET, Biosurface Technologies Corporation, MT, USA) was used (MDFR). The modified design allowed placement of customized sample carriers on the bottom of each drip flow cell. To minimize the risk of microbial contamination of the MDFR, all tubing and trays were sterilized in an autoclave before assembly. Each cell was inoculated with 1 ml *S. mutans* suspension in early log phase to allow bacteria adhesion. After six hours, a constant flow of sterile nutrient broth was provided with a multi-channel controlled peristaltic pump (Masterflex L/S controller and Ismatec ISM184 pump). A mature biofilm formed while the reactor operated for an additional 15 to 20 hours with a constant flow rate at 50 ml/hr and the temperature was maintained at 37° C. During continuous flow, the biofilm experienced very low shear caused by the gravity flow of media dripping onto a surface set at a 10° angle. At the end of the 15 to 20 hours, biofilm accumulation was quantified by removing a sample from the reactor channels, rinsing the sample to remove the planktonic cells, scraping the biofilm from the sample and performing bacterial viability test using LIVE/DEAD® BacLight™ kit.

Bacterial Viability

LIVE/DEAD® BacLight™ Bacterial Viability kit was used to quantitatively distinguish live and dead bacteria in a mixed bacterial population. The viability of the bacterial populations was assessed as a function of the membrane integrity of the cell after incubating for about 24 hours to 48 hours, comparing treated versus untreated samples. Cells with a compromised membrane were considered to be dead or dying if the cells appeared red (R) after staining, whereas cells with an intact membrane that appeared green (G) after staining were considered to be live.

The excitation/emission maxima for the dyes were about 480/500 nm (emission 1; green) for SYTO 9 stain and 490/635 nm (emission 2; red) for propidium iodide. The background remained virtually nonfluorescent. The two dye components provided with the LIVE/DEAD BacLight Bacterial Viability Kits had a 1:1 mixture to provide good live/dead discrimination. The excitation/emission of stained bacteria was measured in a fluorescence microplate reader. The data was analyzed by dividing the fluorescence intensity of the stained bacterial suspensions ($F_{cell}$) at emission 1 (em1) by the fluorescence intensity at emission 2 (em2). The $Ratio_{G/R}$ versus percentage of live cells in the bacterial suspension was plotted.

$Ratio_{G/R} = Fcell, em1/Fcell, em2$

Sample Storage: Real Time (Long-Term) Antimicrobial Activity Test and Accelerated Shelf Life for Mechanical Properties For 'real-time' testing, polymer samples prepared according to the Formulae below were stored in artificial saliva at 37° C., for the periods of 24 hour, 1 month, 2 month, 3 months, 6 months (at 37° C. in incubated shaker).

To test time-periods of 6 months, 1 year or more than 1 year, samples were aged by storing in accelerated conditions in an incubator held at 50° C. and 55% relative humidity (RH). The time-periods for storage in accelerated conditions were determined by Accelerated Aging Time (ATT) calculations, herein. For example, it was determined that samples aged for 52 days in the above-mentioned accelerated storage conditions were equivalent to samples aged at ambient conditions for about 1 year.

The samples were removed from storage conditions for testing antimicrobial activity and flexural strength.

Artificial saliva was prepared according to Macknight-Hane and Whitford (1992) formula. The saliva was formed by dissolving 2 g methyl-p-hydroxybenzoate in 800 ml distilled water. 10 g of sodium carboxymethyl cellulose was dissolved into 200 ml of distilled boiling water, and then mixed with the methyl-p-hydroxybenzoate solution until it formed a gel. Each of the following compounds were individually dissolved in the methyl-p-hydroxybenzoate solution and added to the gel in the following order: 0.625 g of KCl, 0.059 g $MgCl_2 \cdot 6H_2O$, 0.166 g of $CaCl_2) \cdot 2H_2O$, 0.804 g of $K_2HPO_4$, 0.326 g of $KH_2PO_4$ each dissolved in methyl-p-hydroxybenzoate solution, and mixed well. The pH of artificial saliva was adjusted to 6.75 with 1N KOH.

Accelerated Aging (Long Term Shelf Life) Test:

The accelerated Aging test for antimicrobial denture device was according to the Standard Guide for Accelerated Aging of Sterile Barrier Systems for Medical Devices-ASTM F1980-07 (Reapproved 2011). Accelerated aging test assumed that the chemical reactions involved in the deterioration of materials followed the Arrhenius reaction rate function in which a 10° C. increase, or decrease, in temperature results in, approximately, a two times, or ½-time, change, respectively, in the rate of a chemical reaction ($Q_{10}$). The Arrhenius equation wherein $Q_{10}$ equal to 2, a common and conservative means of calculating an aging factor, was used. An accelerated aging factor (AAF) estimate was calculated by the following equation:

$AAF = Q_{10}^{[AA-TRT)/10]}$, where: $T_{AA}$ is accelerated aging temperature (° C.) and $T_{RT}$ is ambient temperature (° C.).

The accelerated aging time (AAT) needed to establish equivalence to real time aging was determined by dividing the desired (or required) shelf life by the AAF.

Accelerated Aging Time(AAT)=Desired(RT)/AAF.

An accelerated aging protocol was followed using a conservative aging factor, where $Q_{10}=2$, using aging test time intervals for example, as follows: time zero, 6 months, 1 year, 2 years, 3 years and 5 years. Test conditions, room temperature $T_{RT}=22°$ C., test temperature $T_{AA}=50°$ C., both dried and 55% relative humidity conditions were defined. Because denture base material is normally used in high relative humidity level in the mouth, 50° C./55% RH was chosen as equivalent to the environments for a denture base life cycle. Test duration was calculated using the defined $Q_{10}$, $T_{RT}$ and $T_{AA}$. For example, to calculate ATT for 1 year (365 days) at ambient conditions, where $AAF=2.0^{[(50-22)/10]}=2.0^{2.8}=6.96$, AAT=365 days/6.96=52 days.

An Accelerated Aging equivalent of an aging time interval at room temperature was determined for dental composite materials stored at the selected temperature and humidity for each time-period, as follows: 6 month of room temperature was considered to be equivalent to 26 days of accelerated conditions, 1 year was considered equivalent to 52 days, 2 years was considered equivalent to 104 days, 3 years was considered equivalent to 156 days, and 5 years at room temperature was considered equivalent to 260 days at accelerated conditions.

LIST OF ABBREVIATION

MMA: methyl methacrylate
PMMA: poly(methyl methacrylate)
BDMA: 1,4-butanediol dimethacrylate
BisGMA: 2,2-bis[4-(2-hydroxy-3-methacryloyloxypropyl)-phenyl]propane
UDMA: 1,6-bis(methacryloxy-2-ethoxy-carbonylamino)-2,4,4-trimethylhexane
TEGDMA: triethylene glycol dimethacrylate
SR833s: tricyclododecane dimethanol diacrylate
GDMA: glycerol-dimethacrylate
DMPT: N, N dimethyl-para-toluidine
HQ: Hydroqunione
BPO: Benzoyl peroxide
Ir819: Phenylbis(2,4,6-trimethylbenzoyl)phosphine oxide
CHX: Chlorhexidine Antimicrobial Composite Material Preparation
Formula 1 Through Formula 8: Two-Component (Powder-Liquid) System A. Liquid Resin Mixture and Powder Composite Preparation: Two-part powder component-liquid component systems were prepared as follows.

The liquid part of each two-part system was a homogeneous liquid resin mixture that comprised components (Liquid Part Components), as described in Table 1, and an antimicrobial polymerizable QAMS monomer. The amount of antimicrobial QAMS monomer listed in Table 2, is based on the total weight of antimicrobial polymerizable composition rather than the liquid part. The components were mixed by gentle mechanical stirring at room temperature for 60 minutes.

The antimicrobial polymerizable QAMS monomer (Product K-18, Kimmerling Group) was used in the liquid resin mixture. The antimicrobial monomer was obtained which comprised a quaternary ammonium silane comprising three methacrylate functional groups. In a method for preparation described in Example 26 of U.S. Pat. No. 10,159,630, tetraethoxysiliane (TEOS), methacryloxy propyltrimethoxy silane (3-MPTS) and octadecyldimethoxysilyl propyl ammonium chloride (SiQAC) were mixed in a molar ratio of about 1:3:1. The mixture was hydrolyzed by adding stoichiometric molar concentrations of MilliQ water at pH 2.5, followed by a condensation reaction at pH 7.4 by monitoring the pH and adding 1N NaOH to adjust the pH of the mixture with a combination pH electrode. After the reaction was completed, the solvent was removed by vacuum and dried under high vacuum to obtain the antimicrobial QAMS monomer, which was used to make the liquid components, as described above.

The powder part of the two-part systems were well-dispersed powder mixtures containing powder part components, as listed in Table 1, and further comprising SSHZP antimicrobial filler (having 10 wt % silver ion, Selected Silver® Zr2K) or zinc oxide silica (provided by Sukgyung-gAT Co. Ltd.). The weight percent of antimicrobial filler listed in Table 2 was based on the total weight of the antimicrobial polymerizable composition. The components were mixed in a long roll jar mill (U.S. Stoneware). Five mm or 12 mm ceramic balls were used for milling powder mixtures for 30 minutes with a frequency of rotation of 80 rpm.

B. Sample Preparation.

Sample composite materials were polymerized as follows. The liquid parts prepared above were mixed with the powder parts at 2:3 mass ratio. The two-part mixtures were stirred thoroughly for about 30 seconds to 45 seconds to ensure complete wetting of the powder, and homogenous liquid mixtures were achieved.

The composite mixtures were poured into molds, as specified by the International Organization for Standardization according to ISO-20795-1, and allowed to harden for about 2 minutes at ambient conditions. The mold/denture flasks were then placed in a pressure cooker for further polymerization at about 40° C. to 50° C., and about 0.15 MPa to about 0.20 MPa pressure for about 20 minutes. The polymerized antimicrobial composite samples were removed from the mold/denture flask. Test samples of the resin systems were prepared in accordance with the test method, and as described above.

TABLE 1

Two-Component Antimicrobial Polymerizable Compositions.

| | Ingredients | wt % | Ratio |
|---|---|---|---|
| Liquid Part Components | MMA | 89 | 2 parts |
| | BDMA | 10 | |
| | DMPT | 1 | |
| | HQ | 0.1 | |
| Total weight percent | | 100 | |
| Powder Part Components | PMMA | 89 | 3 parts |
| | BPO | 1 | |
| | Glass Fillers | 10 | |
| | Pigments/fiber | 0.2 | |
| Total weight percent | | 100 | |

TABLE 2

Antimicrobial Polymerizable Compositions For Making Composites.

| Cold Cured Denture Base | Control (wt %) | Formula 1 (wt %) | Formula 2 (wt %) | Formula 3 (wt %) | Formula 4 (wt %) | Formula 5 (wt %) | Formula 6 (wt %) | Formula 7 (wt %) | Formula 8 (wt %) |
|---|---|---|---|---|---|---|---|---|---|
| Liquid Part Components (Table 1) | 40 | 36.0 | 36.0 | 36.0 | 36.0 | 36.0 | 40.0 | 36.0 | 35.0 |
| Powder Part Components (Table 1) | 60 | 59.75 | 59.5 | 59.0 | 58.5 | 58.0 | 58.0 | 60.0 | 55.0 |
| Antimicrobial QAMS monomer | 0 | 4.0 | 4.0 | 4.0 | 4.0 | 4.0 | 0 | 4.0 | 5.0 |
| SSHZP filler | 0 | 0.25 | 0.5 | 1.0 | 1.5 | 2.0 | 2.0 | 0 | 0 |
| ZnO/SiO$_2$ | 0 | 0 | 0 | 0 | 0 | 0 | 0 | 0 | 5 |

Formula 9: One Component System (Liquid) System (Light Cured)

A. Liquid Polymer Resin Composite Preparation: A one component, light curable liquid system was prepared that was suitable for use in a three-dimensional (3D) printing system. A homogenous mixture was formed by mixing BisGMA, TEGMA, GDMA, the antimicrobial QAMS monomer prepared above, fillers, including SSHZP antimicrobial particle filler (containing 10 wt % silver, Selected-Silver® Zr2K from Milliken & Company), Ir819 (bisacrylphosphine oxide), color pigment (FeO), and 0.01 wt % BHT, according to Table 3. The components were mixed using a spin-mixer to form homogenous mixtures.

B. Sample Preparation: The homogenous mixtures were suitable for use in 3D printing via a digital light process (DLP) method (using MoonRAY Model S by SprintRay, and/or NextDent 5100, by 3D Systems). Test specimen were prepared by three-dimensional printing having dimensions required by test method protocols.

TABLE 3

Light-Cured 3D Printed Denture With Antimicrobial Additives

| Ingredients | Control (wt %) | Formula 9 (wt %) |
|---|---|---|
| BisGMA | 40 | 35 |
| TEGDMA | 40 | 40 |
| GDMA | 6 | 4 |
| antimicrobial QAMS monomer | 0 | 4 |
| SSHZP filler | 0 | 2 |
| Silanated SiO2 glass | 7 | 8 |
| BaO/SiO/BO glass | 5 | 5 |
| Glass Fiber | 1 | 1 |
| Ir819 | 1 | 1 |
| Color pigments | <0.5 | <0.5 |

Samples prepared according to Formulae 1, 2, 5, 8, and 9, were tested at 24 hours for antimicrobial activity against *S. mutans*, *C. albicans*, *P. gingivalis*, and *L. casei*, according to Antimicrobial Test—ASTM E2180 (2017). Sample discs were prepared having 30 mm diameter and 1.0 mm in thickness, with varying concentrations of SSZHP antimicrobial filler as indicated in Table 2 and Table 3, or with zinc oxide silicate filler. The results are reported in Table 4.

TABLE 4

Effectiveness of Dental Materials For Reducing Microbial Growth (24 Hours Contact).

| Formula | *S. mutans* (% red) (24 hr) | *C. albicans* (% red) (24 hr) | *P. gingivalis* (% red) (24 hr) | *L. casei* (% red) (24 hr) |
|---|---|---|---|---|
| Control | 0 | 0 | 0 | 0 |
| Positive Control (5% CHX) | >>99.99 | >>99.99 | NA | NA |
| Formula 1 (SSHZP 0.25 wt %) | 99.89 | 61.29 | 99.9 | 99 |
| Formula 2 (SSHZP 0.5 wt %) | 99.99 | 98.0 | 99.9 | 99.9 |
| Formula 5 (SSHZP 2 wt %) | >99.99 | >99.99 | NA | NA |
| Formula 8 (ZnO/SiO$_2$ 5 wt %) | >99.99 | 93.0% | 99.99 | 99.97 |
| Formula 9 (SSHZP 2 wt %) | >>99.99 | 99.75 | NA | NA |

Samples prepared according to Formula 1 through Formula 5, were tested at 24 hours, and stored samples were tested monthly, up to 6 months storage in standard non-accelerated conditions, for antimicrobial activity against *S. mutans* and *C. albicans* according to Antimicrobial Test—ASTM E2180 (2017). Sample discs were prepared having 30 mm diameter and 1.0 mm in thickness, with varying concentrations of SSZHP antimicrobial filler as indicated in Table 2. The results were reported in Table 5, and graphically represented in FIG. 1, for activity against *S. mutans*. The results were reported in Table 6, and graphically represented in FIG. 2, for activity against *C. albicans*. Reduction in the growth of *S. mutans* and *C. albicans*, was compared to the control sample which had no SSZHP and no antimicrobial QAMS monomer.

TABLE 5

Antimicrobial Activity Of Denture Material With Varying Concentrations Of Antimicrobial Filler For Reducing *S. mutans* (CFU/ml).

| Time | control | Formula 1 (SSHZP 0.25 wt %) | Formula 2 (SSHZP 0.5 wt %) | Formula 3 (SSHZP 1 wt %) | Formula 4 (SSHZP 1.5 wt %) | Formula 5 (SSHZP 2 wt %) |
|---|---|---|---|---|---|---|
| 24 hours | 1.24E+05 | 1.31E+02 | 10E+00 | 0 | 7.43E+00 | 0 |
| 1 month | 1.51E+05 | 3.38E+04 | 1.84E+04 | 6.96E+03 | 0 | 0 |
| 2 months | 1.38E+05 | 2.66E+02 | 1.71E+03 | 9.29E+02 | 0 | 9.28E+00 |
| 3 months | 2.09E+05 | 1.72E+05 | 1.16E+05 | 9.96E+04 | 1.86E+01 | 0 |
| 4 months | 5.08E+04 | 3.74E+04 | 3.41E+04 | 4.73E+04 | 0 | 2.15E+00 |
| 5 months | 1.80E+05 | 1.46E+05 | 1.33E+05 | 1.53E+05 | 4.64E+00 | 0 |
| 6 months | 2.20E+05 | 2.01E+05 | 1.64E+05 | 1.43E+05 | 1.07E+01 | 0 |

TABLE 6

Antimicrobial Activity Of Denture Material With Varying Concentrations Of Antimicrobial Filler For Reducing *C. albicans* (CFU/ml).

| Time | control | Formula 1 (SSHZP 0.25 wt %) | Formula 2 (SSHZP 0.5 wt %) | Formula 3 (SSHZP 1 wt %) | Formula 4 (SSHZP 1.5 wt %) | Formula 5 (SSHZP 2 wt %) |
|---|---|---|---|---|---|---|
| 24 hours | 1.12E+07 | 6.18E+03 | 6.03E+03 | 1.33E+04 | 6.18E+03 | 6.03E+03 |
| 1 month | 1.38E+07 | 4.88E+06 | 2.74E+05 | 1.00E+04 | 7.79E+03 | 8.76E+03 |
| 2 months | 1.58E+07 | 3.16E+06 | 1.85E+04 | 9.15E+03 | 3.03E+03 | 2.79E+03 |
| 3 months | 1.01E+07 | 9.38E+06 | 2.06E+05 | 7.49E+03 | 7.14E+03 | 9.78E+03 |
| 4 months | 2.33E+07 | 9.24E+06 | 1.26E+07 | 4.57E+06 | 9.12E+03 | 7.32E+03 |
| 5 months | 6.25E+06 | 2.85E+06 | 2.92E+06 | 1.05E+04 | 2.15E+3 | 1.57E+04 |
| 6 months | 1.34E+07 | 1.35E+07 | 1.28E+07 | 1.25E+07 | 2.28E+03 | 2.69E+03 |

Samples were tested for antimicrobial activity at 24 hours, and monthly for 5 months, for samples of Formula 5 having both SSZHP filler (2 wt %) and antimicrobial QAMS monomer (4 wt %). The results were compared to samples of Formula 6 having SSZHP filler (2 wt %) and no antimicrobial monomer, and samples of Formula 7 with antimicrobial QAMS monomer (4 wt %) and no SSZHP filler. Samples were prepared and tested against a control having neither SSZHP filler nor the antimicrobial QAMS monomer, according to Antimicrobial Test—ASTM E2180 (2017). The growth of *S. mutans* and *C. albicans*, reported in CFU/ml, are reported in Table 7, and graphically presented in FIG. 3 and FIG. 4.

TABLE 7

Antimicrobial Activity Comparison Of Combined and Individual Additives.

| | *C. albicans* (CFU/ml) | | | | *S. mutans* (CFU/ml) | | | |
|---|---|---|---|---|---|---|---|---|
| Time | control | Formula 5 (QAMS/ SSHZP) | Formula 6 (SSHZP) | Formula 7 (QAMS) | control | Formula 5 (QAMS/ SSHZP) | Formula 6 (SSHZP) | Formula 7 (QAMS) |
| 24 hours | 1.12E+07 | 4.05E+03 | 1.52E+04 | 8.96E+06 | 1.24E+05 | 0.00E+00 | 7.37E+02 | 2.27E+03 |
| 1 month | 1.38E+07 | 8.28E+03 | 5.19E+03 | 1.22E+07 | 1.51E+05 | 0.00E+00 | 0.00E+00 | 1.18E+04 |
| 2 months | 1.58E+07 | 4.69E+03 | 4.82E+03 | 1.01E+07 | 1.38E+05 | 1.35E+02 | 1.12E+05 | 2.58E+04 |
| 3 months | 1.01E+07 | 1.04E+04 | 8.12E+06 | 1.41E+07 | 2.09E+05 | 1.87E+02 | 2.69E+04 | 4.69E+04 |
| 4 months | 9.24E+06 | 7.30E+03 | 2.95E+05 | 5.96E+06 | 1.38E+05 | 1.43E+03 | 3.74E+03 | 1.56E+05 |
| 5 months | 1.34E+07 | 1.57E+04 | 3.90E+06 | 1.39E+07 | 2.20E+05 | 2.14E+04 | 2.86E+04 | 1.75E+05 |

Formula 5, comprising a polymer sample made with a combination of 4 wt % QAMS (antimicrobial monomer) and 2 wt % SSHZP filler, showed long-term effectiveness against both *C. albicans* and *S. mutans*, compared to the control, Formula 6 and Formula 7. Formula 7, having no SSHZP antimicrobial filler, showed little effectiveness against *C. albicans*. Surprisingly, Formula 5 having the combination of the antimicrobial monomer and the SSHZP filler displayed a synergistic effect with unexpectedly long term, high reduction in growth of *C. albicans*, compared to Formula 6 having the same amount of SSHZP antimicrobial filler, with no antimicrobial QAMS monomer. Moreover, Formula 5 displayed a synergistic effect with unexpectedly long term, high reduction in growth of *S. mutans*, compared to Formula 7, comprising the antimicrobial QAMS monomer.

*S. mutans* biofilm growth was tested using a modified drip flow reactor, and samples of Formula 5, were compared to Formula 6, Formula 7 and a control, for 20 hours. The samples were tested for bacterial viability by LIVE/DEAD® BacLight™ Bacterial Viability kit. The results of percent live detectable are reported in Table 8. The single biofilm activities for polymer samples Formula 5 which is made with a combination of 4 wt % antimicrobial QAMS monomer and 2 wt % SSHZP, and Formula 6 made with 2 wt % SSHZP alone, antimicrobial for 20 hours, showed significant reduction of *S. mutans* biofilm formation on the surface compared to Formula 7 (comprising 4 wt % QAMS alone) and the control.

TABLE 8

Biofilm Activity Comparison of Combined and Individual Additives.

| Formula# | *S. mutans* Biofilm Live/Dead-% live detectable |
|---|---|
| control | 100 |
| Formula 5 (QAMS/SSHZP) | 0 |
| Formula 6 (SSHZP) | 0 |
| Formula 7 (QAMS) | 50.2 |

Four-month aged (in artificial saliva for 4 months at 37° C.) denture material samples of Formula 4 and Formula 5 were prepared to test for *S. mutans* biofilm growth. The *S.* mutans biofilm was formed by placing denture disc in nutrition medium for 48 hours at 37° C. in shaking incubator, then both the media and sample surfaces were tested by using_LIVE/DEAD® BacLight™ Bacterial Viability kit. The in-vitro data indicated that Formula 5 had reduced more than 90% of *S. mutans* in nutrition medium, and Formula 4 had reduced 78%, while untreated control showed a 15% reduction. Discs prepared according to Formula 4, showed a reduction in biofilm growth of *S. mutans* of 97% when tested on the denture disc surface (showing less than 3% of live *S. mutans*), while no live *S. mutans* was detected in surface testing of discs made from Formula 5, whereas the untreated control had 24% live *S. mutans*. The results are reported graphically, in FIG. 5.

Long term antimicrobial activity of composites samples of Formula 5 was tested, from 24 hours to 6 months using non-accelerated testing. Data at 1 year, 3 years to 5 years were acquired through accelerated testing, according to the accelerated protocol provided herein. Formula 5, comprising a polymer material prepared from 2 wt % antimicrobial filler (SSHZP, with 10 wt % silver) and 4 wt % antimicrobial QAMS monomer showed significant reduction in microbial activity for *C. albicans* and *S. mutans* compared to the control, throughout the real-time and accelerated testing periods. The results are reported in Table 9, and, also, graphically represented in FIG. 6 (*C. albicans*) and FIG. 7 (*S. mutans*).

Formula 5 showed long-term reduction in growth of *S. mutans* and *C. albicans* in accelerated aging studies. A 3 log reduction or greater in microbial growth was demonstrated for Formula 5 compared to the control, up to 5 years accelerated testing periods for both *S. mutans* and *C. albicans*.

The release of silver ion content from denture material was measured over time. Samples were prepared by forming 20 g rectangular bar (53 mm×62 mm×5 mm) comprising the two-component cold cured polymer material according to Formula 5 and Formula 6. The sample materials comprised either a combination of antimicrobial QAMS monomer and SSHZP antimicrobial filler (Formula 5) or only antimicrobial filler (SSHZP) (Formula 6).

The samples were soaked in artificial saliva (330 ml), and conditioned in a shaker at 37° C. shaker for periods of time between 2 hours and 48 hours. At each time period, a 30 ml solution was removed from the shaker and tested for silver ion concentration by Inductively Coupled Plasma Mass Spectrometry (ICP-MS). No solution was added to replace the removed solution. The amount of detected silver (reported in ppb) is provided in Table 10 and FIG. 8. The combination of the antimicrobial QAMS monomer and SSHZP filler (SelectedSilver® Zr2K) demonstrated a slower release of silver ions than a polymeric denture material having SSHZP without the antimicrobial monomer.

TABLE 9

Long term Antimicrobial Activity Against *C. albicans* and *S. mutans*.

| Time Period | *C. albicans* (CFU/ml) | | *S. mutans* (CFU/ml) | |
| --- | --- | --- | --- | --- |
| | Control | Formula 5 (QAMS/SSHZP) | Control | Formula 5 (QAMS/SSHZP) |
| 24 hours | 1.10E+07 | 6.18E+03 | 6.92E+04 | 7.43E+00 |
| 1 months | 1.30E+07 | 8.76E+03 | 4.35E+04 | 0.00E+00 |
| 2 months | 9.23E+06 | 2.79E+03 | 2.18E+05 | 9.28 |
| 3 months | 8.50E+06 | 9.78E+03 | 4.05E+04 | 0 |
| 4 months | 8.28E+06 | 7.32E+03 | 1.52E+05 | 2.15 |
| 6 months | 1.48E+07 | 5.93E+03 | 3.73E+04 | 2.15 |
| *1 year | 1.09E+07 | 1.04E+04 | 6.98E+04 | 2.92E+01 |
| *3 years | 1.27E+07 | 7.22E+03 | 1.38E+05 | 8.72E+02 |
| *4 years | 1.12E+07 | 8.46E+04 | 1.12E+05 | 4.12E+01 |
| *5 years | 1.26E+07 | 1.17E+04 | 1.11E+05 | 0 |

*Accelerated

TABLE 10

Release Of Silver Ion From Polymeric Material Over Time.

| Time (hour) | Formula 5 (QAMS/SSHZP) (ppb) | Formula 6 (SSHZP) (ppb) |
| --- | --- | --- |
| 2 | 2 | 7 |
| 5 | 10 | 18 |
| 9 | 24 | 33 |
| 24 | 20 | 31 |
| 33 | 22 | 31 |
| 48 | 21 | 27 |

Properties of flexural strength, modulus, solubility, sorption and residual MMA were tested for Formulae 2, 5 through 7, and 9, according to the methods provided herein.

TABLE 11

Flexural Strength, Modulus, And Solubility for Cold Cured and Light Cured Dentures.

| Example | Flexural Strength (MPa) | Modulus (MPa) | SOLUBILITY (μg/mm³) | SORPTION (μg/mm³) | MMA residual (% mass) |
| --- | --- | --- | --- | --- | --- |
| Two-component acrylate commercial denture material | 73.89 | 2510 | 1.74 | 21.85 | 1.25% |
| Formula 5 | 68 | 2485 | 0.795 | 26.285 | 1.30% |
| Formula 2 | 69 | 2400 | 1.27 | 27.45 | 1.14% |
| Formula 6 | 73 | 2500 | 1.02 | 25.55 | |
| Formula 7 | 64 | 2000 | 1.52 | 27.89 | |
| ISO 20795-1 requirements for cold cure denture | >60 | >1500 | <8.0 | <32 | <4.5 |
| Commercially available light cure denture material | 80.81 | 2945 | 0.04 | 27.53 | NA |

TABLE 11-continued

Flexural Strength, Modulus, And Solubility for Cold Cured and Light Cured Dentures.

| Example | Flexural Strength (MPa) | Modulus (MPa) | SOLUBILITY (µg/mm$^3$) | SORPTION (µg/mm$^3$) | MMA residual (% mass) |
|---|---|---|---|---|---|
| Formula 9 (light cured) | 74.03 | 2774.5 | 1.25 | 31.61 | NA |
| ISO 20795-1 requirements for light cure denture | >65 | >2000 | <1.6 | <32 | <2.2 |

Properties of flexural strength and modulus were tested on samples having accelerated aging. Sample bars were tested at 48 hours, and after accelerated aging by storage at 50° C. in dry oven for a time equivalent to real time aging up to one year. Formula 5 and control, and tested according to the methods provided herein. The mechanical properties of Formula 5 at 48 hours, and aged samples did not show a significant decreased in terms of flexural strength and modulus. The results, and corresponding ISO 201795 requirements, are reported in Table 11, and graphically illustrated in FIGS. 9 and 10.

We claim:

1. A method of making an intraoral device that reduces bacterial growth and biofilm formation, comprising:
 a. providing a mixture of resin components comprising
  i. a plurality of polymerizable (meth)acrylate monomers; and
  ii. antimicrobial particles; and
  iii. an initiator;
 b. forming the mixture into the dimensions of the intraoral device using a three-dimensional printing method; and
 c. light curing the mixture using the three-dimensional printing method to obtain the intraoral device.

2. The method of claim 1, wherein the antimicrobial particles comprise silver oxide, silver carbonate, silver zeolite, zinc oxide, copper oxide, titanium oxide, or a combination of the foregoing.

3. The method of claim 1, wherein the antimicrobial particles comprise a silver-emitting ceramic.

4. The method of claim 3, wherein the antimicrobial particles comprise silver sodium hydrogen zirconium phosphate.

5. The method of claim 4, wherein the silver sodium hydrogen zirconium phosphate comprises between 3 wt % and 10 wt % silver metal ion.

6. The method of claim 1, wherein the antimicrobial particles have a size of between 1 nm and 5 µm.

7. The method of claim 1, wherein the antimicrobial particles have a size of between 1 nm and 3 µm.

8. The method of claim 1, wherein the antimicrobial particles have a size of between 1 nm and 1 µm.

9. The method of claim 1, wherein the mixture of resin components further comprises an antimicrobial monomer comprising a quaternary ammonium compound (QAC) group.

10. The method of claim 9, wherein the antimicrobial monomer comprises a silane, silicate, siloxane, or silanol group.

11. The method of claim 9, wherein the antimicrobial monomer comprises a quaternary ammonium silane having an acrylate or methacrylate group.

12. The method of claim 9, wherein the antimicrobial monomer comprises quaternary ammonium methacryloxy silicate.

* * * * *